(12) United States Patent
Kolczewski et al.

(10) Patent No.: US 7,989,628 B2
(45) Date of Patent: *Aug. 2, 2011

(54) 2-AMINOQUINOLINES

(75) Inventors: Sabine Kolczewski, Loerrach (DE); Claus Riemer, Freiburg (DE); Olivier Roche, Folgensbourg (FR); Lucinda Steward, Basel (CH); Juergen Wichmann, Steinen (DE); Thomas Woltering, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 65 days.

This patent is subject to a terminal disclaimer.

(21) Appl. No.: 12/394,083

(22) Filed: Feb. 27, 2009

(65) Prior Publication Data

US 2009/0227628 A1    Sep. 10, 2009

(30) Foreign Application Priority Data

Mar. 7, 2008  (EP) .................................. 08152435

(51) Int. Cl.
C07D 215/38    (2006.01)

(52) U.S. Cl. ...................................... 546/159; 546/160
(58) Field of Classification Search .................. 546/159, 546/160
See application file for complete search history.

(56) References Cited

U.S. PATENT DOCUMENTS

| 2007/0202924 A1* | 8/2007 | Lai et al. ......................... 455/566 |
| 2007/0299074 A1 | 12/2007 | Netz et al. |
| 2008/0081907 A1* | 4/2008 | Kolczewski et al. ............ 544/98 |
| 2008/0146567 A1* | 6/2008 | Kolczewski et al. ........ 514/235.2 |
| 2009/0227584 A1* | 9/2009 | Kolczewski et al. ........ 514/235.2 |

FOREIGN PATENT DOCUMENTS

| WO | WO 03/037872 | 5/2003 |
| WO | WO 2004/096771 | 11/2004 |
| WO | WO 2005/082871 | 9/2005 |
| WO | WO 2008/037626 | 4/2008 |

OTHER PUBLICATIONS

Giordanetto, Bioorg & Med Chem Lett, vol. 17, pp. 4232-4241, 2007.*
Hoyer et al., Pharmacol. Rev. vol. 46, pp. 157-204 (1994).
Rees et al., FEBS Lett. vol. 355, pp. 242-246 (1994).
Francken et al., Eur. J. Pharmacol. vol. 361, pp. 299-309 (1998).
Noda et al., J. Neurochem. vol. 84, pp. 222-232 (2003).
Thomas, D. R., Pharmacol. Ther. vol. 111(3) pp. 707-714 (2006).
Doly et al., The Journal of Comparative Neurology vol. 476 pp. 316-329 (2004).
Dubertret et al., J. of Psychiatric Research vol. 35 pp. 371-376 (2004).
Garcia-Ladona et al., 36th Annual Meeting Soc. Neurosci. 10/14-10/18, Atlanta Abstract 33.1 (2006).
Drescher et al., 36th Annual Meeting Soc. Neurosci. 10/14-10/18, Atlanta Abstract 33.2 (2006).
Thomas, Neuropharmacology vol. 51(3) pp. 566-577 (2006).
Barnes et al., Neuropharmacology vol. 38 pp. 1083-1152 (1999).
Pasqualetti et al., Mol. Brain Res. vol. 56 pp. 1-8 (1998).
Wang et al., Neurosci. Lett. vol. 278 pp. 9-12 (2000).
Birkett et al., Neuroreport vol. 11 pp. 2017-2020 (2000).
Iwata et al., Mol. Psychiatry vol. 6 pp. 217-219 (2001).
Duncan et al., Brain Research vol. 869, pp. 178-185 (2000).
Sprouse et al., Synapse, vol. 54(2) pp. 111-118 (2004).
Database CA, Chemical Abstracts Service XP002542080 & *Jour. of the Chem. Soc* 227-32 ISSN 0368-1769, 1949.

* cited by examiner

*Primary Examiner* — D Seaman
(74) *Attorney, Agent, or Firm* — George W. Johnston; Patricia S. Rocha-Tramaloni; Kimberly J. Prior

(57) ABSTRACT

The present invention is concerned with 2-aminoquinoline derivatives of formula I

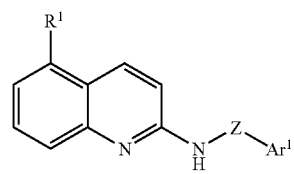

wherein Z, R1, and Ar1 are as defined herein, pharmaceutical compositions containing them, methods for their manufacture. The compounds are 5-HT$_{5A}$ receptor antagonists and are useful in the prevention and/or treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, abuse of drugs, motor disorders such as Parkinson's disease, psychiatric disorders or gastrointestinal disorders.

23 Claims, No Drawings

2-AMINOQUINOLINES

PRIORITY TO RELATED APPLICATION(S)

This application claims the benefit of European Patent Application No. 08152435.7, filed Mar. 7, 2008, which is hereby incorporated by reference in its entirety.

BACKGROUND OF THE INVENTION

The neurotransmitter 5-hydroxytryptamine (5-HT, serotonin) modulates a wide range of physiological and pathological processes in the central nervous system and periphery, including anxiety, sleep regulation, aggression, feeding and depression (Hoyer et al., *Pharmacol. Rev.* 46, 157-204, 1994). Both pharmacological characterization and molecular cloning of several 5-HT receptor genes has revealed that 5-HT mediates its diverse physiological actions through a multiplicity of receptor subtypes. These receptors belong to at least two different protein superfamilies: ligand-gated ion channel receptor ($5-HT_3$) and the G-protein-coupled 7-transmembrane receptors (thirteen distinct receptors cloned to date). In addition, within the G-protein-coupled receptors, serotonin exerts its actions through a multiplicity of signal transduction mechanisms.

The cloning and characterization of the human 5-HT5A serotonin receptor has been described in *FEBS Letters*, 355, 242-246 (1994). The sequence is not closely related to that of any previously known serotonin receptor, with the best homology being 35% to the human $5-HT_{1B}$ receptor. It encodes a predicted 357 amino-acid protein, with seven putative transmembrane domains, consistent with that of a G-protein coupled receptor. The sequence is characterized by containing an intron between transmembrane domains V and VI. More recently coupling to Gi/o α mechanisms has been demonstrated with the inhibition of forskolin stimulated cAMP and also evidence for more complicated G-protein mediated coupling mechanisms have been proposed (Francken et al. *Eur. J. Pharmacol.* 361, 299-309, 1998; Noda et al., *J. Neurochem.* 84, 222-232, 2003). Furthermore, in WO 2004/096771 it is described the use of compounds, which are active on the $5-HT_{5A}$ serotonin receptor for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

The *Pharmacology & Therapeutics*, 111, 707-714 (2006) describes potential therapeutic utility of 5-HT5A receptor ligands for the treatment of circadian rhythm, sleep disturbances, mood disorders, schizophrenia, cognitive disorders and autism. The *Journal of Comparative Neurology*, 476, 316-329 (2004) suggests based on the localisation pattern of the $5-HT_{5A}$ receptor in the rat spinal cord that $5-HT_{5A}$ receptors may play a role in central motor control, nociception and autonomic function such as stress induced urinary incontinence and overactive bladder. The *Journal of Psychiatric Research*, 38, 371-376 (2004) describes evidence for a potential significant role of the $5-HT_{5A}$ gene in schizophrenia and more specifically in patients with later age at onset.

SUMMARY OF THE INVENTION

The present invention provides 2-aminoquinoline derivatives. In particular, the present invention is concerned with compounds of formula (I)

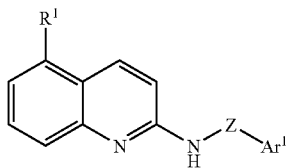

I wherein
Z is a bond, —$CH_2$—, or —$CHCH_3$—;
$R^1$ is alkyl, hydroxyalkyl, haloalkyl, aminoalkyl, cyanoalkyl, cycloalkyl, allyl, -alkylene-C(O)Oalkyl, -alkylene-C(O)NR$^i$R$^{ii}$, —C(N—R$^{iii}$)NR$^{iv}$R$^v$, —C(=N-R$^{iii}$)-cycloalkyl, —C(=N-R$^{iii}$)-alkyl, —O-alkyl, —O-cycloalkyl, —O-alkylene-O-alkyl, —O-alkylene-S(O)$_x$-alkyl, or —NR$^a$R$^b$, wherein R$^a$ and R$^b$ are each independently H, alkyl, cycloalkyl, -alkylene-cycloalkyl, allyl, -alkylene-S(O)$_x$-alkyl, —S(O)$_2$NR$^{vi}$R$^{vii}$, —S(O)$_2$-alkyl, —S(O)$_2$-cycloalkyl, -alkylene-NR$^{viii}$R$^{ix}$, -alkylene-O-alkyl, —C(O)-cycloalkyl, —C(O)alkyl, —C(O)-alkylene-heterocycloalkyl, —C(O)-heterocycloalkyl, —C(O)NR$^{vi}$R$^{viii}$, —C(O)-alkylene-NR$^{viii}$R$^{ix}$, —C(O)-alkylene-O-alkyl, or heterocycloalkyl;
$Ar^1$ is phenyl or a 5- to 10-membered mono- or bicyclic heteroaryl, each unsubstituted or substituted with one or more alkyl, cycloalkyl, alkoxy, haloalkoxy, haloalkyl, halo, OH, CN, $NH_2$, $NO_2$, or having two substituents in the ortho-position that forms a bridge anellated to the aromatic ring, wherein the bridge is selected from the group consisting of —O—$CH_2CH_2$O—, —O—$CHCH_3CH_2$—, and —O—$C(CH_3)_2CH_2$—, and wherein phenyl is not substituted with halo in the para-position;
$R^i$, $R^{ii}$, $R^{vii}$, $R^{viii}$ and $R^{ix}$ are each independently H, alkyl, cycloalkyl, or -alkylene-N(alkyl)$_2$,
$R^{iii}$, $R^{iv}$, and $R^v$ are each independently H, OH or alkoxy; and
x is 0, 1 or 2; wherein
heterocycloalkyl is unsubstituted or substituted with one or more oxo, alkyl, halo, haloalkyl, haloalkoxy, alkoxy, hydroxy, hydroxyalkyl, or CN;
or a pharmaceutically acceptable salt thereof.

The compounds of formula I can contain asymmetric carbon atoms. Accordingly, the present invention includes all stereoisomeric forms of the compounds of formula I, including each of the individual enantiomers and mixtures thereof, i.e. their individual optical isomers and mixtures thereof.

The invention also provides pharmaceutical compositions comprising a therapeutically effective amount of a compound of formula I and a pharmaceutically acceptable carrier. The invention further provides methods for the manufacture of the compounds and compositions of the invention.

Compounds of formula I have good activity on the $5-HT_{5A}$ receptor. Therefore, the invention provides methods for treating depression (which term includes bipolar depression, unipolar depression, single or recurrent major depressive episodes with or without psychotic features, catatonic features, melancholic features, atypical features or postpartum onset, seasonal affective disorders and dysthymia, depressive disorders resulting from a general medical condition including, but not limited to, myocardial infarction, diabetes, miscarriage or abortion), anxiety disorders, (which includes generalized anxiety and social anxiety disorder, panic disorders, agoraphobia, social phobia, obsessive compulsive disorders, post-traumatic stress disorders), psychotic disorders (which includes schizophrenia, schizoaffective disorders, bipolar disease, mania, psychotic depression, and other psychoses involving paranoia and delusions), pain (particularly neuropathic pain), memory disorders (including dementia, amnesic disorders and age-associated memory impairment), disorders of eating behaviors (including nervosa and bulimia nervosa), sexual dysfunction, sleep disorders (including disturbances of circadian rhythm, dyssomnia, insomnia, sleep apnea and narcolepsy), withdrawal from abuse of drugs (such as of cocaine, nicotine, benzodiazepines, alcohol (ethanol), caffeine, phencyclidine and phencyclidine-like compounds, opiates such as cannabis, heroin, morphine, sedative hypnotic, amphetamine or amphetamine-related drugs), motor disorders such as Parkinson's disease, dementia in Parkinson's disease, neuroleptic-induced Parkinsonism and tardive dyskinesias, as well as other psychiatric disorders and gastrointestinal disorders such as irritable bowel syndrome (WO 2004/096771).

The preferred indications with regard to the present invention are the treatment of anxiety, depression, sleep disorders and schizophrenia.

DETAILED DESCRIPTION OF THE INVENTION

The following definitions of general terms used herein apply irrespective of whether the terms in question appear alone or in combination. It must be noted that, as used in the specification and the appended claims, the singular forms "a", "an," and "the" include plural forms unless the context clearly dictates otherwise.

As used herein, the term "alkyl" denotes monovalent linear or branched saturated hydrocarbon moiety, consisting solely of carbon and hydrogen atoms, having from 1 to 7 carbon atoms, for example, methyl, ethyl, propyl, isopropyl, n-butyl, iso-butyl, sec-butyl, tert-butyl and the like. Preferred alkyl groups are groups with 1, 2, 3 or 4 carbon atoms.

As used herein, the term "alkylene" means a linear saturated divalent hydrocarbon radical of one to seven carbon atoms or a branched saturated divalent hydrocarbon radical of three to seven carbon atoms. Preferred are divalent hydrocarbon radicals of one to four carbon atoms. In case alkylene is located in between two heteroatoms, it is preferably from 2 to 7 carbon atoms, more preferably from 2 to 4 carbon atoms.

As used herein, the term "allyl" denotes a group —$CH_2CH=CH_2$.

The term "halo" denotes chloro, iodo, fluoro and bromo. Preferred halo are fluoro, chloro and bromo, more preferred are fluoro and chloro.

The term "haloalkyl" denotes an alkyl group as defined above wherein at least one of the hydrogen atoms of the alkyl group is replaced by a halogen atom, preferably fluoro or chloro, most preferably fluoro. Examples of haloalkyl include, but are not limited to, methyl, ethyl, propyl, isopropyl, isobutyl, sec-butyl, tert-butyl, pentyl or n-hexyl wherein one or more hydrogen atoms are replaced by Cl, F, Br or I atom(s), as well as those haloalkyl groups specifically illustrated by the examples herein below. Among the preferred haloalkyl groups are monofluoro-, difluoro- or trifluoro-methyl, -ethyl or -propyl, for example 3,3,3-trifluoropropyl, 2-fluoroethyl, 2,2,2-trifluoroethyl, fluoromethyl, trifluoromethyl.

The term "hydroxyalkyl" denotes an alkyl group as defined above wherein at least one of the hydrogen atoms of the alkyl group is replaced by a hydroxy group. Examples of hydroxyalkyl include, but are not limited to, methyl, ethyl, propyl, isopropyl, isobutyl, sec-butyl, tert-butyl, pentyl or n-hexyl wherein one or more hydrogen atoms are replaced by OH, as well as those hydroxyalkyl groups specifically illustrated by the examples herein below.

The term "cyanoalkyl" denotes an alkyl group as defined above wherein at least one of the hydrogen atoms of the alkyl group is replaced by a cyano group. Examples of cyanoalkyl include, but are not limited to, methyl, ethyl, propyl, isopropyl, isobutyl, sec-butyl, tert-butyl, pentyl or n-hexyl wherein one or more hydrogen atoms are replaced by CN, as well as those cyanoalkyl groups specifically illustrated by the examples herein below.

The term "aminoyalkyl" denotes an alkyl group as defined above wherein at least one of the hydrogen atoms of the alkyl group is replaced by a amino group, i.e. a —$NH_2$ group. Examples of aminoalkyl include, but are not limited to, methyl, ethyl, propyl, isopropyl, isobutyl, sec-butyl, tert-butyl, pentyl or n-hexyl wherein one or more hydrogen atoms are replaced by —$NH_2$, as well as those groups specifically illustrated by the examples herein below.

The term "alkoxy" denotes a group —O—R' wherein R' is alkyl as defined above.

The term "haloalkoxy" denotes an alkoxy group as defined above wherein at least one of the hydrogen atoms of the alkyl group is replaced by a halogen atom, preferably fluoro or chloro, most preferably fluoro.

The term "anellated", "annellated", "annulated", "fused" or "condensed" denotes the attachment of a further ring to an existing ring via a common single or double bond, i.e. both rings share one single or double bond. Annular residues are hence constructed from side-on condensed cyclic segments.

The term "aromatic" means the presence of an electron sextet in a ring, according to Hückel's rule.

The term "cycloalkyl" refers to a monovalent saturated monocyclic hydrocarbon radical of 3 to 7 ring carbon atoms, such as cyclopropyl, cyclobutanyl, cyclopentyl, cyclohexyl or cycloheptyl. Preferred are cyclopropyl, cyclopentyl and cyclohexyl. Cycloalkyl is optionally substituted as described herein.

The term "heterocycloalkyl" refers to a monovalent saturated 5- to 6-membered monocyclic ring system containing one, two or three ring heteroatoms selected from N, O and S, the remaining ring atoms being carbon atoms. "Heterocycloalkyl" may be unsubstituted or substituted as described herein. Examples of heterocycloalkyl moieties include, but are not limited to, pyrrolidinyl, tetrahydrothiophenyl, tetrahydropyranyl, tetrahydrothiopyranyl, piperidinyl, piperazinyl, morpholinyl, or thiomorpholinyl. Preferred examples are tetrahydropyranyl, tetrahydrothiopyranyl or piperidinyl. Examples for substituents on heterocycloalkyl include, but are not limited to, oxo, alkyl, halo, haloalkyl, haloalkoxy, alkoxy, hydroxy, hydroxyalkyl, or CN. Preferred substituents are oxo or alkyl.

The term "heteroaryl" as defined herein denotes a monovalent monocyclic or bicyclic aromatic ring system of 5 to 10 ring atoms containing one, two, or three ring heteroatoms selected from N, O, and S, the remaining ring atoms being C. Examples of heteroaryl moieties include, but are not limited to, thiophenyl, furanyl, pyrrolyl, imidazolyl, pyrazolyl, oxazolyl, isoxazolyl, thiazolyl, isothiazolyl, [1,2,4]oxadiazolyl, [1,3,4]oxadiazolyl, [1,2,4]triazolyl, [1,2,3]triazolyl, tetrazolyl, pyridinyl, pyrimidinyl, pyrazinyl, pyridazinyl, indolyl, benzofuranyl or benzothiofuranyl. Preferred examples for heteroaryl are furanyl and benzofuranyl. The heteroaryl may be optionally substituted as defined herein, and the substituents are in principle the same as those for phenyl. Examples for substituents on heteroaryl include, but are not limited to, alkyl, cycloalkyl, alkoxy, haloalkoxy, haloalkyl, halo, OH, CN, $NH_2$, $NO_2$, or an anellated bridge being selected from —O—$CH_2CH_2O$—, —O—CHCH$_3$CH$_2$—, and —O—C(CH$_3$)$_2$CH$_2$—. A preferred substituent on heteroaryl is alkyl.

The term "thiophenyl" as used herein is synonymous with "thienyl" and denotes a thiophene substituent, i.e., C$_4$H$_4$S.

Analogously to the heteroaryl system, phenyl can be unsubstituted or substituted with one or more substituents selected from alkyl, cycloalkyl, alkoxy, haloalkoxy, haloalkyl, halo, OH, CN, NH$_2$, NO$_2$, and an anellated bridge being selected from —O—CH$_2$CH$_2$O—, —O—CHCH$_3$CH$_2$—, and —O—C(CH$_3$)$_2$CH$_2$—, however, wherein phenyl is not para-substituted with halo. Preferred substituents on phenyl are alkyl, cycloalkyl, alkoxy, haloalkoxy, or an anellated bridge being selected from —O—CH$_2$CH$_2$O—, —O—CHCH$_3$CH$_2$—, and —O—C(CH$_3$)$_2$CH$_2$—.

When indicating the number of subsituents, the term "one or more" means from one substituent to the highest possible number of substitution, i.e. replacement of one hydrogen up to replacement of all hydrogens by substituents. Thereby, one, two or three substituents are preferred.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

"Therapeutically effective amount" means an amount that is effective to prevent, alleviate or ameliorate symptoms of disease or prolong the survival of the subject being treated.

In detail, the present invention relates to compounds of the general formula (I)

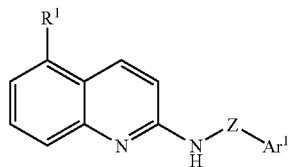

I wherein
Z is a bond, —CH$_2$—, or —CHCH$_3$—;
R$^1$ is alkyl, hydroxyalkyl, haloalkyl, aminoalkyl, cyanoalkyl, cycloalkyl, allyl, -alkylene-C(O)Oalkyl, -alkylene-C(O)NR$^i$R$^{ii}$, —C(N—R$^{iii}$)NR$^{iv}$R$^v$, —C(=N—R$^{iii}$)-cycloalkyl, —C(=N—R$^{iii}$)-alkyl, —O-alkyl, —O-cycloalkyl, —O-alkylene-O-alkyl, —O-alkylene-S(O)$_x$-alkyl, or —NR$^a$R$^b$, wherein R$^a$ and R$^b$ are each independently H, alkyl, cycloalkyl, -alkylene-cycloalkyl, allyl, -alkylene-S(O)$_x$-alkyl, —S(O)$_2$NR$^{vi}$R$^{vii}$, —S(O)$_2$-alkyl, —S(O)$_2$-cycloalkyl, -alkylene-NR$^{viii}$R$^{ix}$, -alkylene-O-alkyl, —C(O)-cycloalkyl, —C(O)alkyl, —C(O)-alkylene-heterocycloalkyl, —C(O)-heterocycloalkyl, —C(O)NR$^{vi}$R$^{vii}$, —C(O)-alkylene-NR$^{viii}$R$^{ix}$, —C(O)-alkylene-O-alkyl, or heterocycloalkyl;
Ar$^1$ is phenyl or a 5- to 10-membered mono- or bicyclic heteroaryl, each unsubstituted or substituted with one or more alkyl, cycloalkyl, alkoxy, haloalkoxy, haloalkyl, halo, OH, CN, NH$_2$, NO$_2$, or having two substituents in the ortho-position that forms a bridge anellated to the aromatic ring, wherein the bridge is selected from —O—CH$_2$CH$_2$O—, —O—CHCH$_3$CH$_2$—, and —O—C(CH$_3$)$_2$CH$_2$—, and wherein phenyl is not substituted with halo in para-position;
R$^i$, R$^{ii}$, R$^{vii}$, R$^{viii}$ and R$^{ix}$ are each independently H, alkyl, cycloalkyl, or -alkylene-N(alkyl)$_2$;
R$^{iii}$, R$^{iv}$, and R$^v$ are each independently H, OH or alkoxy; and
x is 0, 1 or 2; wherein
heterocycloalkyl is unsubstituted or substituted with one or more oxo, alkyl, halo, haloalkyl, haloalkoxy, alkoxy, hydroxy, hydroxyalkyl, or CN,
or a pharmaceutically acceptable salt thereof.

It is to be understood that the expression "Ar$^1$ is phenyl or a 5- to 10-membered mono- or bicyclic heteroaryl" means that the attachment of Ar$^1$ is on the aromatic ring.

In certain embodiments of the compound of formula I, R$^1$ is as described above.

In certain embodiments of the compound of formula I,
R$^1$ is alkyl, hydroxyalkyl, haloalkyl, aminoalkyl, cyanoalkyl, cycloalkyl, allyl, -alkylene-C(O)Oalkyl, -alkylene-C(O)NR$^i$R$^{ii}$, —C(N—R$^{iii}$)NR$^{iv}$R$^v$,
—O-alkyl, —O-cycloalkyl, —O-alkylene-O-alkyl, —O-alkylene-S(O)$_x$-alkyl, or —NR$^a$R$^b$, wherein R$^a$ and R$^b$ are each independently H, alkyl, cycloalkyl, -alkylene-cycloalkyl, allyl, -alkylene-S(O)$_x$-alkyl, —S(O)$_2$NR$^{vi}$R$^{vii}$, —S(O)$_2$-alkyl, —S(O)$_2$-cycloalkyl, -alkylene-NR$^{viii}$R$^{ix}$, -alkylene-O-alkyl, or heterocycloalkyl;
R$^i$, R$^{ii}$, R$^{vii}$, R$^{viii}$ and R$^{ix}$ are each independently H, alkyl, cycloalkyl, or -alkylene-N(alkyl)$_2$;
R$^{iii}$, R$^{iv}$, and R$^v$ are each independently H, OH or alkoxy; and
x is 0, 1 or 2, wherein
heterocycloalkyl is unsubstituted or substituted with one or more oxo, alkyl, halo, haloalkyl, haloalkoxy, alkoxy, hydroxy, hydroxyalkyl, or CN.

In certain embodiments of the compound of formula I,
R$^1$ is alkyl, hydroxyalkyl, allyl, -alkylene-C(O)Oalkyl, -alkylene-C(O)NR$^i$R$^{ii}$, —C(N—R$^{iii}$)NR$^{iv}$R$^v$, —O-alkyl, —O-alkylene-O-alkyl, —O-alkylene-S(O)$_x$-alkyl,
or —NR$^a$R$^b$, wherein R$^a$ and R$^b$ are each independently H, alkyl, allyl, -alkylene-S(O)$_x$-alkyl, —S(O)$_2$NR$^{vi}$R$^{vii}$, —S(O)$_2$-cycloalkyl, -alkylene-O-alkyl, or heterocycloalkyl;
R$^i$, R$^{ii}$, R$^{vi}$ and R$^{vii}$ are each independently H, alkyl, cycloalkyl, or alkylene-N(alkyl)$_2$;
R$^{iii}$, R$^{iv}$, and R$^v$ are each independently H, OH or alkoxy; and
x is 0, 1 or 2, wherein
heterocycloalkyl is unsubstituted or substituted with one or more oxo, alkyl, halo, haloalkyl, haloalkoxy, alkoxy, hydroxy, hydroxyalkyl, or CN.

In certain embodiments of the compound of formula I, R$^i$, R$^{ii}$, R$^{vi}$, R$^{vii}$, R$^{viii}$ and R$^{ix}$ are each independently H, alkyl, cycloalkyl, or -alkylene-N(alkyl)$_2$, preferably alkyl.

In certain embodiments of the compound of formula I, R$^{iii}$, R$^{iv}$, and R$^v$ are each independently H, OH or alkoxy, preferably H or OH.

In certain embodiments of the compound of formula I, heterocycloalkyl is unsubstituted or substituted with one or more oxo, alkyl, halo, haloalkyl, haloalkoxy, alkoxy, hydroxy, hydroxyalkyl, or CN. Preferably, the substituents are oxo or alkyl.

In certain embodiments of the compound of formula I, heterocycloalkyl is selected from the group consisting of pyrrolidinyl, tetrahydrothiophenyl, tetrahydropyranyl, tetrahydrothiopyranyl, piperidinyl, piperazinyl, morpholinyl, and thiomorpholinyl. Preferred heterocycloalkyl are tetrahydropyranyl, tetrahydrothiopyranyl and piperidinyl. Optional substituents are as defined above.

In certain embodiments of the compound of formula I, Z is a bond or —CH$_2$—.

In certain embodiments of the compound of formula I, Ar$^1$ is as defined above.

In certain embodiments of the compound of formula I,
Ar$^1$ is phenyl or a 5- to 10-membered mono- or bicyclic heteroaryl, each unsubstituted or substituted with one or more alkyl, cycloalkyl, alkoxy, haloalkoxy, haloalkyl, OH, CN, NH$_2$, NO$_2$, or having two substituents in the ortho-position that form a bridge anellated to the aromatic ring, wherein the bridge is selected from —O—CH$_2$CH$_2$O—, —O—CHCH$_3$CH$_2$—, and —O—C(CH$_3$)$_2$CH$_2$—.

In certain embodiments of the compound of formula I,
Ar$^1$ is phenyl or a 5- to 10-membered mono- or bicyclic heteroaryl, each unsubstituted or substituted with one or more alkyl, cycloalkyl, alkoxy, haloalkoxy, or having two substituents in the ortho-position that form a bridge anellated to the aromatic ring, wherein the bridge is selected from —O—CH$_2$CH$_2$O—, —O—CHCH$_3$CH$_2$—, and —O—C(CH$_3$)$_2$CH$_2$—.

In certain embodiments of the compound of formula I,
Ar$^1$ is phenyl or a 5- to 10-membered mono- or bicyclic heteroaryl,
  wherein phenyl is unsubstituted or substituted with one or more alkyl, cycloalkyl, alkoxy, haloalkoxy, haloalkyl, OH, CN, NH$_2$, NO$_2$, or having two substituents in the ortho-position that form a bridge anellated to the aromatic ring, wherein the bridge is selected from —O—CH$_2$CH$_2$O—, —O—CHCH$_3$CH$_2$—, and —O—C(CH$_3$)$_2$CH$_2$—, and
  wherein the 5- to 10-membered mono- or bicyclic heteroaryl is unsubstituted or substituted with one or more alkyl, cycloalkyl, alkoxy, haloalkoxy, halo, haloalkyl, OH, CN, NH$_2$, or NO$_2$.

In certain embodiments of the compound of formula I,
Ar$^1$ is phenyl or a 5- to 10-membered mono- or bicyclic heteroaryl,
  wherein phenyl is unsubstituted or substituted with one or more alkyl, cycloalkyl, alkoxy, haloalkoxy, or having two substituents in the ortho-position that form a bridge anellated to the aromatic ring, wherein the bridge is selected from —O—CH$_2$CH$_2$O—, —O—CHCH$_3$CH$_2$—, and —O—C(CH$_3$)$_2$CH$_2$—, and
  wherein the 5- to 10-membered mono- or bicyclic heteroaryl is unsubstituted or substituted with one or more alkyl, cycloalkyl, alkoxy, or haloalkoxy.

In certain embodiments of the compound of formula I, the 5- to 10-membered mono- or bicyclic heteroaryl is selected from the group consisting of thiophenyl, furanyl, pyrrolyl, imidazolyl, pyrazolyl, oxazolyl, isoxazolyl, thiazolyl, isothiazolyl, [1,2,4]oxadiazolyl, [1,3,4]oxadiazolyl, [1,2,4]triazolyl, [1,2,3]triazolyl, tetrazolyl, pyridinyl, pyrimidinyl, pyrazinyl, pyridazinyl, indolyl, benzofuranyl and benzothiofuranyl. Preferred heteroaryl are furanyl or benzofuranyl. Heteroaryl is optionally substituted as defined above.

Preferred Ar$^1$ are 5-methyl-furan-2-yl, 2-methoxy-phenyl, 2-methyl-benzofuran-7-yl, 2-trifluoromethoxy-phenyl, 2-methyl-2,3-dihydro-benzofuran-7-yl, 2,2-dimethyl-2,3-dihydro-benzofuran-7-yl, or 3-cyclopropyl-phenyl.

It is understood that all combinations of the specifically described embodiments above are encompassed by present invention.

Preferred compounds of formula I are those as shown in the examples below.

More preferred compounds of formula I are:
N$^2$-(2-methoxy-benzyl)-quinoline-2,5-diamine,
N$^2$-(5-methyl-furan-2-ylmethyl)-quinoline-2,5-diamine,
N$^2$-(5-methyl-furan-2-ylmethyl)-N$^5$-(tetrahydro-pyran-4-yl)-quinoline-2,5-diamine,
N$^2$-(5-methyl-furan-2-ylmethyl)-N$^5$-(2-methylsulfanyl-ethyl)-quinoline-2,5-diamine,
N$^5$-(2-methanesulfinyl-ethyl)-N$^2$-(5-methyl-furan-2-ylmethyl)-quinoline-2,5-diamine,
N$^2$-(2-trifluoromethoxy-benzyl)-quinoline-2,5-diamine,
N$^2$-(2-methyl-benzofuran-7-yl)-quinoline-2,5-diamine,
N$^2$-(2-methyl-2,3-dihydro-benzofuran-7-yl)-quinoline-2,5-diamine,
N$^2$-(2,2-dimethyl-2,3-dihydro-benzofuran-7-yl)-quinoline-2,5-diamine,
N$^2$-(3-cyclopropyl-phenyl)-quinoline-2,5-diamine,
N,N-dimethyl-N'-(2-{[(5-methyl-2-furyl)methyl]amino}quinolin-5-yl)sulfamide,
N,N-dimethyl-N'-{2-[(2-methyl-2,3-dihydro-benzofuran-7-yl)amino]quinolin-5-yl}sulfamide,
4-{2-[(5-methyl-furan-2-ylmethyl)-amino]-quinolin-5-yl}-butan-1-ol, and
N-hydroxy-2-(2-methoxy-benzylamino)-quinoline-5-carboxamidine.

The present compounds of formula I, their starting materials, their pharmaceutically acceptable salts, and their optical isomers can be prepared by methods known in the art.

For example, a process to synthesize representative compounds of formula I

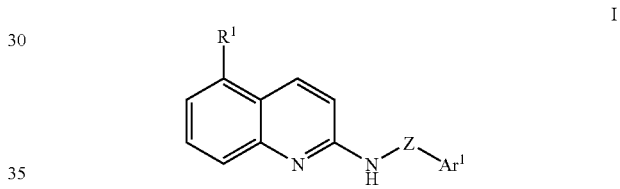

can be used which comprises one of the following steps:
a) reacting a compound 2

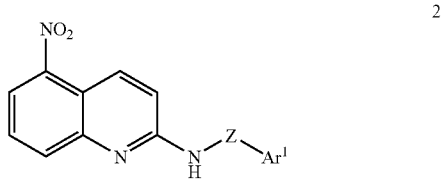

with hydrogen in the presence of a palladium catalyst to give a compound of formula 1 with R$^1$ being —NR$^a$R$^b$ wherein R$^a$ and R$^b$ are H;
b) reacting a compound 4

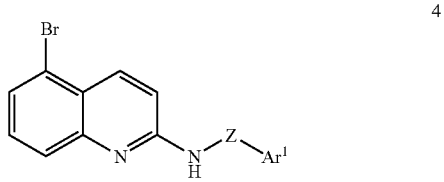

b1) with an amine of formula R$^a$R$^b$NH in a palladium catalyzed substitution reaction, wherein R$^a$ and R$^b$ are independently selected from H, alkyl, allyl, cycloalkyl, -alkylene-cycloalkyl, allyl, -alkylene-alkyl, -alkylene-NR$^{viii}$R$^{ix}$, -alkylene-O-alkyl, and heterocycloalkyl, to give a compound of formula I wherein $R^1$ is —$NR^aR^b$ and wherein $R^a$ and $R^b$ are each independently H, alkyl, allyl, cycloalkyl, -alkylene-cycloalkyl, allyl, -alkylene-alkyl, -alkylene-$NR^{viii}R^{ix}$, -alkylene-O-alkyl, or heterocycloalkyl; preferably, $R^a$ is H;

b2) with vinyltributyltin in a palladium catalyzed reaction to give the compound of formula I wherein $R^1$ is allyl;

c) reacting a compound of formula 10

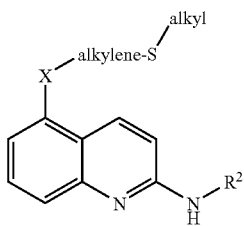

10 wherein X is NH or O and n is from 1 to 7, with meta-chloroperbenzoic acid to obtain a compound of formula I wherein $R^1$ is —$NR^aR^b$ and wherein $R^a$ is H and $R^b$ is -alkylene-$S(O)_x$-alkyl, with x being 1 or 2;

d) reacting a compound of formula I with $R^1$ being $NH_2$ with either a compound of formula $R^bSO_2Cl$ or a compound of formula $R^{vi}R^{vii}NSO_2Cl$ to give a compound of formula I wherein $R^1$ is —$NR^aR^b$ with $R^a$ being H and $R^b$ being —$S(O)_2$-alkyl, —$S(O)_2$-cycloalkyl or —$S(O)_2NR^{iv}R^v$; wherein $R^{iv}$ and $R^v$ are each independently H, alkyl, cycloalkyl or -alkylene-N(alkyl)$_2$;

e) reacting a compound of formula 9

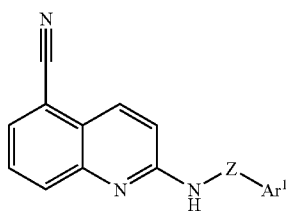

9 with hydroxylamine, to give a compound of formula I wherein $R^1$ is —C(=N—OH)$NH_2$;

f) reacting a compound of formula 7

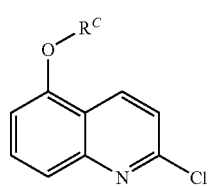

7 wherein $R^C$ is alkyl, alkylene-O-alkyl, or alkylene-S-alkyl with an amine of formula $Ar^1ZNH_2$, and wherein $Ar^1$ and Z are defined above, to give a compound of formula I wherein $R^1$ is —O-alkyl, —O-alkylene-O-alkyl, or -O-alkylene-S-alkyl.

It can be stated that present invention also encompasses the products produced by the above-given processes.

As mentioned earlier, the compounds of formula I and their pharmaceutically acceptable addition salts possess valuable pharmaceutical properties. Compounds of the present invention are active on the 5-$HT_{5A}$ receptor and therefore suitable for the treatment of depression, anxiety disorders, schizophrenia, panic disorders, agoraphobia, social phobia, obsessive compulsive disorders, post-traumatic stress disorders, pain, memory disorders, dementia, disorders of eating behaviors, sexual dysfunction, sleep disorders, withdrawal from abuse of drugs, motor disorders such as Parkinson's disease, psychiatric disorders or gastrointestinal disorders.

Test Description

A [$^3$H]LSD radioligand binding assay was used to determine the affinity of the compounds for the recombinant human 5-$HT_{5A}$ receptor, in membranes from transiently (cDNA) expressed 5-$HT_{5A}$ receptors in Human Embryonic Kidney-EBNA (HEK-EBNA) cells. Assay buffer consisted of Tris (50 mM) buffer containing 1 mM EGTA, 10 mM $MgCl_2$ (pH 7.4) and 10 µM pargyline. The binding assay was carried out in 96-well-plates in the presence of [$^3$H]LSD (approximately 1 nM), approximately 2 µg/well of membrane protein, and 0.5 mg of Ysi-poly-1-lysine SPA beads in a final volume of 200 µl of buffer. Non-specific binding was defined using methiothepin 2 µM. Compounds were tested at 10 concentrations. All assays were conducted in duplicate and repeated at least two times. Assay plates were incubated for 120 min at room temperature before centrifugation. Bound ligand was determined using a Packard Topcount scintillation counter. $IC_{50}$ values were calculated using a non-linear curve fitting program and Ki values calculated using the Cheng-Prussoff equation.

The activity of the compounds according to the invention is exemplified in the table 1 below:

| Example | Ki/nM |
|---------|-------|
| 1 | 27.3 |
| 2 | 83.8 |
| 7 | 92.0 |
| 9 | 81.2 |
| 10 | 99.3 |
| 13 | 93.9 |
| 14 | 112.2 |
| 15 | 49.4 |
| 16 | 44.4 |
| 18 | 71.2 |
| 20 | 60.4 |
| 21 | 100.7 |
| 26 | 61.8 |
| 30 | 219.5 |
| 32 | 44.7 |

The present invention also provides pharmaceutical compositions containing compounds of the invention, for example, compounds of formula I or pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic carriers. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The most preferred indications in accordance with the present invention are those, which include disorders of the central nervous system, for example the treatment of anxiety, depression, sleep disorders and schizophrenia.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

| Tablet Formulation (Wet Granulation) | | | | |
|---|---|---|---|---|
| | | mg/tablet | | |
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| Capsule Formulation | | | | |
|---|---|---|---|---|
| | | mg/capsule | | |
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

Preparation of the Compounds of Present Invention:
Compounds of formula I may be prepared in accordance with the following routes:

Route 1 is Described in Example 1

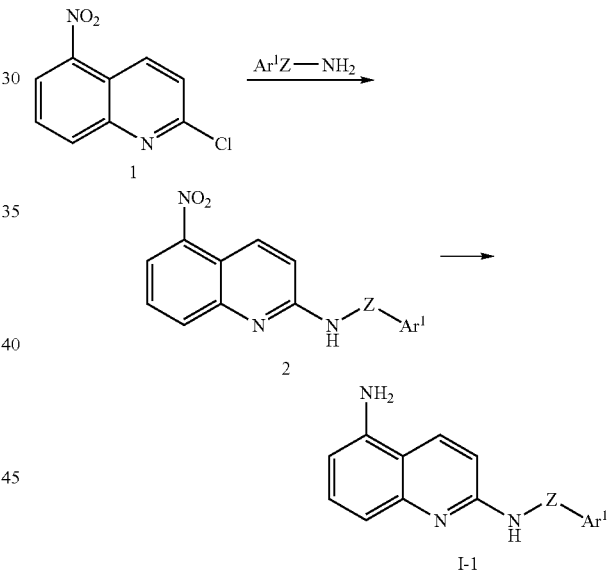

2-Chloro-5-nitro-quinoline (1) is reacted with 2 equivalents of an amine ($Ar^1Z$—$NH_2$) without solvent. Intermediate (2) is reduced with hydrogen in the presence of a palladium catalyst to produce I-1. Z and $Ar^1$ are as defined herein.

Route 2 is Described in Example 3

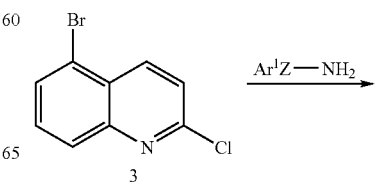

13
-continued

14
Route 4 is Described in Example 19

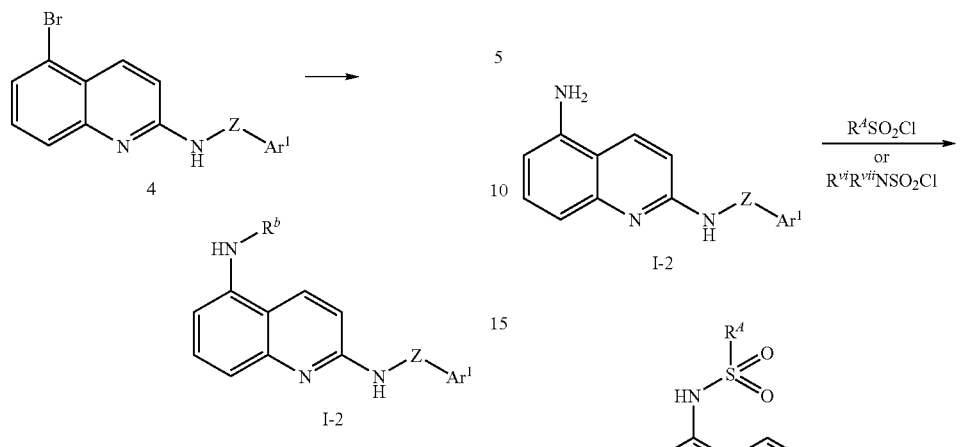

5-Bromo-2-chloro-quinoline (3) is reacted with 2 equivalents of an amine ($Ar^1Z$—$NH_2$) without solvent. Intermediate (4) is reacted with a second amine ($R^bNH_2$) in a palladium catalyzed substitution reaction to produce I-2. $R^b$, Z and $Ar^1$ are as defined herein.

Route 3 is Described in Example 10 and 11

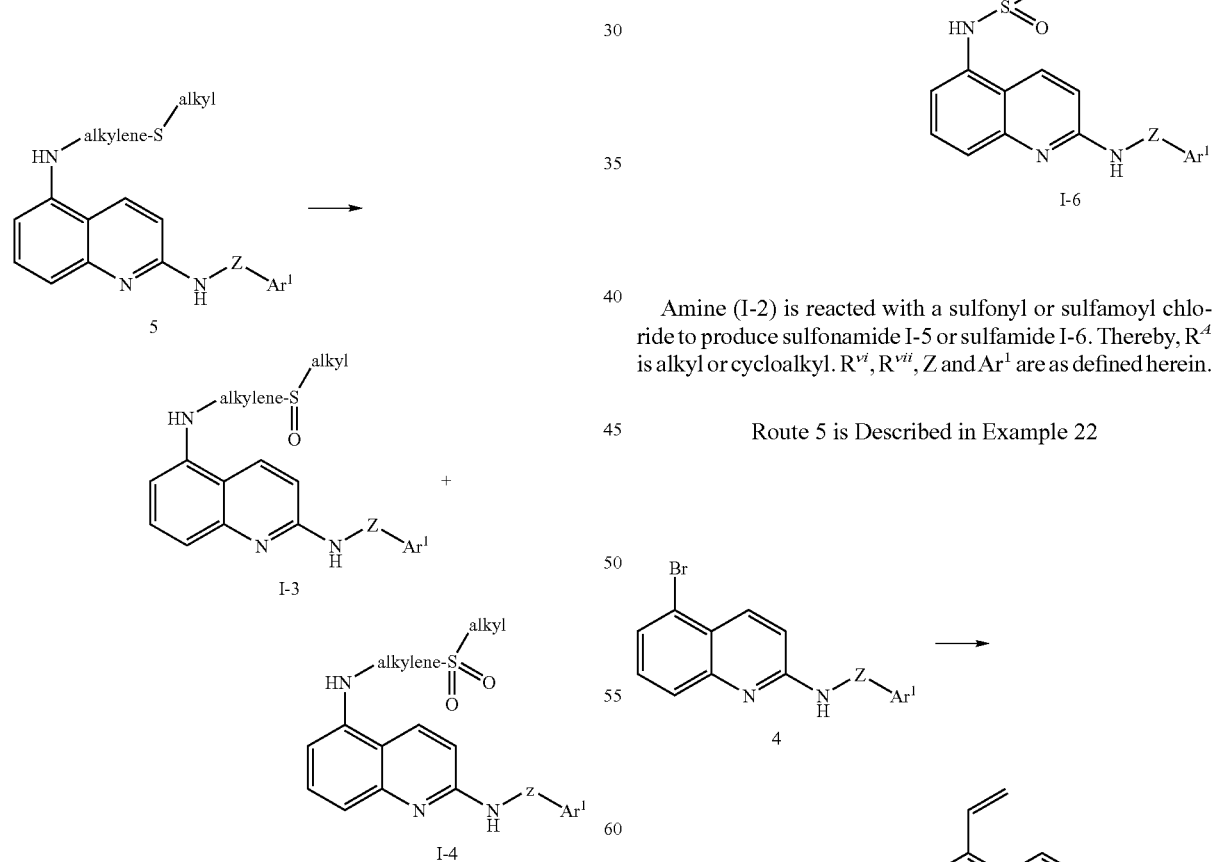

Sulfide (5) is reacted with 2 equivalents of meta-chloroperbenzoic acid to obtain a mixture of the corresponding sulfoxide (1-3) and sulfon (1-4) which could be separated by column chromatography. Z and $Ar^1$ are as defined herein.

Amine (I-2) is reacted with a sulfonyl or sulfamoyl chloride to produce sulfonamide I-5 or sulfamide I-6. Thereby, $R^A$ is alkyl or cycloalkyl. $R^{vi}$, $R^{vii}$, Z and $Ar^1$ are as defined herein.

Route 5 is Described in Example 22

Intermediate 4 is reacted with vinyltributyltin in a palladium catalyzed substitution reaction to produce the vinyl derivative I-7. Z and Ar¹ are as defined herein.

Route 6 is Described in Example 24

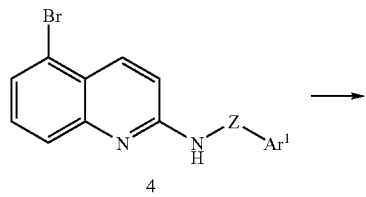

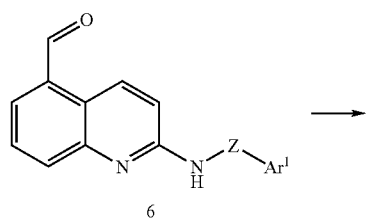

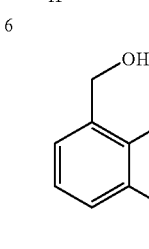

Intermediate 4 is reacted with n-butyllithium and N,N-dimethylformamide to produce the aldehyde 6 which is reduced to the alcohol I-8. Z and Ar¹ are as defined herein.

Route 7 is Described in Example 25

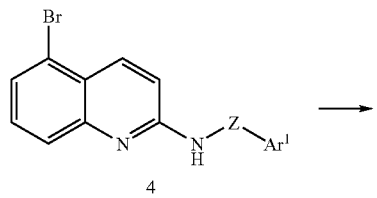

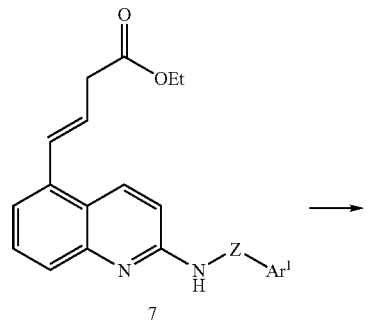

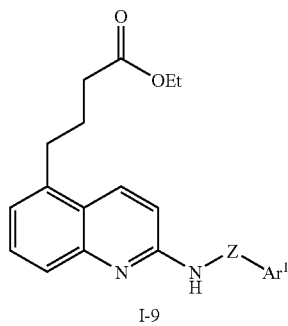

Intermediate 4 is reacted with ethyl-3-butenoate in a palladium catalyzed substitution reaction to produce intermediate 7 which is reduced to the ester I-9. Z and Ar¹ are as defined herein.

Route 8 is Described in Example 26

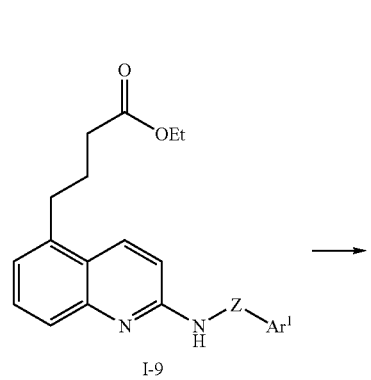

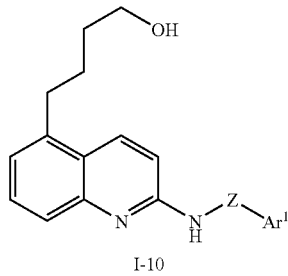

Ester I-9 is reduced to the alcohol I-10 by treatment with lithiumborohydride. Z and Ar¹ are as defined herein.

Route 9 is Described in Example 31

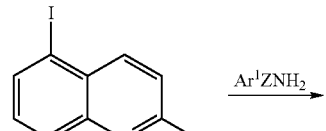

-continued

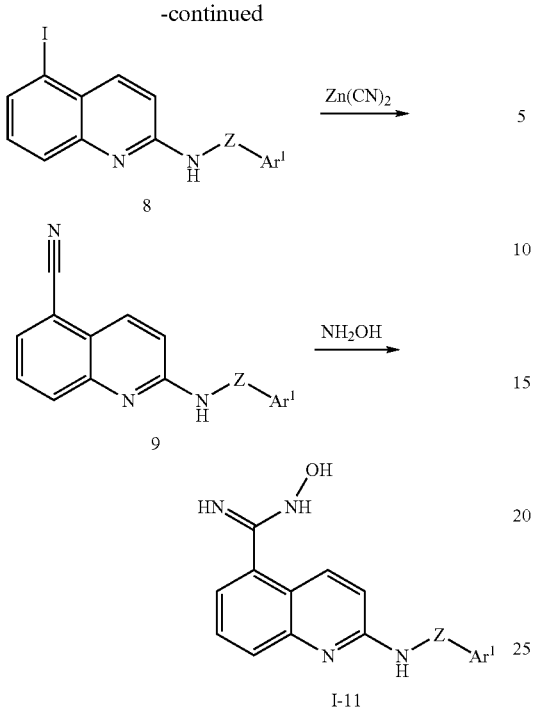

Intermediates 8, prepared from 7 according to route 2, are reacted with zink cyanide in a palladium catalyzed substitution reaction, followed by reaction of cyano derivatives 9 with hydroxylamine to the corresponding amidoximes I-11. Z and $Ar^1$ are as defined herein.

Route 10 is Described in Example 28

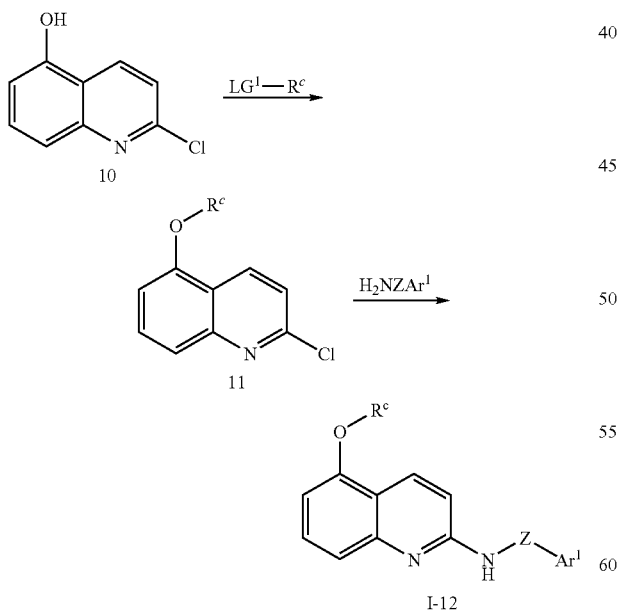

Compound 10 (CAS-RN: 124467-35-2) is reacted with $LG^1$-$R^C$, for instance with bromo-ethyl-methylether to yield intermediate 11 which then is treated with an amine to yield final product I-12. Thereby $R^C$ is selected from alkyl, alky- lene-O-alkyl, and alkylene-S-alkyl, $Ar^1$ is as defined above and $LG^1$ is halo, preferably Br or CL.

EXAMPLES

Example 1

$N^2$-(2-Methoxy-benzyl)-quinoline-2,5-diamine

Step A: 5-Nitro-2-chloroquinoline (CAS 13067-94-2, 3 g, 14 mmol) and 2-methoxy-benzylamine (4.2 g, 31 mmol) were stirred in a sealed tube at 120° C. overnight. The reaction mixture was purified by flash chromatography on silica gel (heptane/ethyl acetate 100:0->30:70 gradient). (2-Methoxy-benzyl)-(5-nitro-quinolin-2-yl)-amine was obtained as a yellow solid (2.2 g, 50%), MS: m/e=310.1 (M+H$^+$).

Step B: (2-Methoxy-benzyl)-(5-nitro-quinolin-2-yl)-amine (2.2 g, 7.1 mmol) was dissolved in 100 mL methanol. Palladium on charcoal (10%, 150 mg, 0.14 mmol) was added and the reaction mixture war hydrogenated with a hydrogen balloon overnight. The palladium was filtered off and the solvent was evaporated. The title compound was obtained as a yellow solid (1.98 g, 100%), MS: m/e=280.4 (M+H$^+$).

Example 2

$N^2$-(5-Methyl-furan-2-ylmethyl)-quinoline-2,5-diamine

The title compound, MS: m/e=254.4 (M+H$^+$), was prepared in accordance with the general method of example 1 from 5-nitro-2-chloroquinoline and 5-methyl-2-furanmethanamine.

Example 3

$N^2$-(5-Methyl-furan-2-ylmethyl)-$N^5$-(1-methyl-piperidin-4-yl)-quinoline-2,5-diamine Step A: 5-Bromo-2-chloroquinoline (CAS 99455, 2.2 g, 9 mmol) and 5-methyl-2-furanmethanamine (2.2 g, 20 mmol) were stirred in a sealed tube at 120° C. overnight. The reaction mixture was purified by flash chromatography on silica gel (heptane/ethyl acetate 100:0->80:20 gradient). (5-Bromo-quinolin-2-yl)-(5-methyl-furan-2-ylmethyl)-amine was obtained as a light brown solid (2.67 g, 92%), MS: m/e =317.1 and 319.0 (M+H$^+$).

Step B: (5-Bromo-quinolin-2-yl)-(5-methyl-furan-2-ylmethyl)-amine (150 mg, 0.47 mmol) was dissolved in 2 mL dioxane. Argon was bubbled through the solution for 2 minutes to remove oxygen. 4-Amino-1-methyl-piperidine (165 mg, 1.45 mmol), sodium tert.-butylate (117 mg, 1.22 mmol), 1,1'-bis(diphenylphosphin)ferrocen (41 mg, 0.074 mmol) and 1,1'-bis(diphenylphosphin)ferrocen-palladium(II)chloride (19 mg, 0.023 mmol) were added. The reaction mixture was stirred in a sealed tube at 120° C. overnight. The solvent was evaporated and the residue purified by flash chromatography on silica gel (dichloromethane/methanol/ammonia 100:0:0->90:10:1 gradient). The title compound was obtained as a brown solid (36 mg, 22%), MS: m/e=351.3 (M+H$^+$).

Example 4

$N^5$-(2-Methoxy-ethyl)-$N^2$-(5-methyl-furan-2-ylmethyl)-quinoline-2,5-diamine

The title compound, MS: m/e=312.3 (M+H+), was prepared in accordance with the general method of example 3 from 5-bromo-2-chloroquinoline, 5-methyl-2-furanmethanamine and 2-methoxy-ethylamine.

Example 5

N$^5$-Methyl-N$^2$-(5-methyl-furan-2-ylmethyl)-quinoline-2,5-diamine

The title compound, MS: m/e=268.4 (M+H$^+$), was prepared in accordance with the general method of example 3 from 5-bromo-2-chloroquinoline, 5-methyl-2-furanmethanamine and methylamine (solution in ethanol).

Example 6

N$^5$-Allyl-N$^2$-(5-methyl-furan-2-ylmethyl)-quinoline-2,5-diamine

The title compound, MS: m/e=294.4 (M+H$^+$), was prepared in accordance with the general method of example 3 from 5-bromo-2-chloroquinoline, 5-methyl-2-furanmethanamine and allylamine.

Example 7

N$^2$-(5-Methyl-furan-2-ylmethyl)-N$^5$-(tetrahydro-pyran-4-yl)-quinoline-2,5-diamine The title compound, MS: m/e=338.4 (M+H$^+$), was prepared in accordance with the general method of example 3 from 2-chloro-5-iodo-quinoline (CAS 455955-26-7), 5-methyl-2-furanmethanamine and 4-amino-tetrahydropyran.

Example 8

N$^5$-(3-Methoxy-propyl)-N$^2$-(5-methyl-furan-2-ylmethyl)-quinoline-2,5-diamine The title compound, MS: m/e=326.4 (M+H$^+$), was prepared in accordance with the general method of example 3 from 5-bromo-2-chloroquinoline, 5-methyl-2-furanmethanamine and 3-methoxy-propylamine.

Example 9

N$^2$-(5-Methyl-furan-2-ylmethyl)-N$^5$-(2-methylsulfanyl-ethyl)-quinoline-2,5-diamine The title compound, MS: m/e=328.4 (M+H$^+$), was prepared in accordance with the general method of example 3 from 2-chloro-5-iodo-quinoline (CAS 455955-26-7), 5-methyl-2-furanmethanamine and 1-(methylthio)-ethylamine.

Example 10:

N$^5$-(2-Methanesulfinyl-ethyl)-N$^2$-(5-methyl-furan-2-ylmethyl)-quinoline-2,5-diamine N$^2$-(5-Methyl-furan-2-ylmethyl)-N$^5$-(2-methylsulfanyl-ethyl)-quinoline-2,5-diamine (200 mg, 0.61 mmol) were dissolved in 6.5 mL dichloromethane and meta-chloro-perbenzoic acid was added (220 mg, 1.3 mmol). The reaction mixture was stirred at room temperature overnight. The reaction mixture was quenched by addition of 10 mL water and 10 mL 2N sodium carbonate solution. The mixture was extracted three times with ethyl acetate (50 mL each). The organic phases ware pooled, dried with sodium sulfate, filtered and evaporated. The reaction mixture was purified by flash chromatography on silica gel (dichloromethane/methanol 100:0→90:10 gradient). The title compound was obtained as a white solid (60 mg, 29%), MS: m/e=344.3 (M+H$^+$) together with N$^5$-(2-methanesulfonyl-ethyl)-N$^2$-(5-methyl-furan-2-ylmethyl)-quinoline-2,5-diamine.

Example 11

N$^5$-(2-Methanesulfonyl-ethyl)-N$^2$-(5-methyl-furan-2-ylmethyl)-quinoline-2,5-diamine N$^2$-(5-Methyl-furan-2-ylmethyl)-N$^5$-(2-methylsulfanyl-ethyl)-quinoline-2,5-diamine (200 mg, 0.61 mmol) were dissolved in 6.5 mL dichloromethane and meta-chloro-perbenzoic acid was added (220 mg, 1.3 mmol). The reaction mixture was stirred at room temperature overnight. The reaction mixture was quenched by addition of 10 mL water and 10 mL 2N sodium carbonate solution. The mixture was extracted three times with ethyl acetate (50 mL each). The organic phases ware pooled, dried with sodium sulfate, filtered and evaporated. The reaction mixture was purified by flash chromatography on silica gel (dichloromethane/methanol 100:0->90:10 gradient). The title compound was obtained as a light yellow foam (37 mg, 17%), MS: m/e=360.1 (M+H$^+$) together with N$^5$-(2-methanesulfinyl-ethyl)-N$^2$-(5-methyl-furan-2-ylmethyl)-quinoline-2,5-diamine.

Example 12

N$^2$-(2-Methyl-benzofuran-7-yl)-N$^5$-(2-methylsulfanyl-ethyl)-quinoline-2,5-diamine The title compound, MS: m/e=364.3 (M+H$^+$), was prepared in accordance with the general method of example 3 from 2-chloro-5-iodo-quinoline (CAS 455955-26-7), (2-methyl-1-benzofuran-7-yl)amine and 1-(methylthio)-ethylamine.

Example 13

N$^2$-(2-Trifluoromethoxy-benzyl)-quinoline-2,5-diamine

The title compound, MS: m/e=334.3 (M+H$^+$), was prepared in accordance with the general method of example 1 from 5-nitro-2-chloroquinoline and 2-(trifluoromethoxy)benzylamine.

Example 14

N$^2$-(2-Methyl-benzofuran-7-yl)-quinoline-2,5-diamine

The title compound, MS: m/e=290.3 (M+H$^+$), was prepared in accordance with the general method of example 1 from 5-nitro-2-chloroquinoline and (2-methyl-1-benzofuran-7-yl)amine.

Example 15

N$^2$-(2-Methyl-2,3-dihydro-benzofuran-7-yl)-quinoline-2,5-diamine

The title compound, MS: m/e=292.0 (M+H$^+$), was prepared in accordance with the general method of example 1 from 5-nitro-2-chloroquinoline and 2,3-dihydro-2-methyl-7-benzofuranamine (CAS 26210-74-2).

Example 16

N²-(2,2-Dimethyl-2,3-dihydro-benzofuran-7-yl)-quinoline-2,5-diamine

The title compound, MS: m/e=306.1 (M+H$^+$), was prepared in accordance with the general method of example 1 from 5-nitro-2-chloroquinoline and 7-amino-2,3-dihydro-2,2-dimethylbenzofuran (CAS 68298-46-4).

Example 17

N²-(2,2-Dimethyl-2,3-dihydro-benzofuran-7-yl)-N⁵-(1,1-dioxo-hexahydro-1λ⁶-thiopyran-4-yl)-quinoline-2,5-diamine The title compound, MS: m/e=438.3 (M+H$^+$), was prepared in accordance with the general method of example 3 from 2-chloro-5-iodo-quinoline (CAS 455955-26-7), 7-amino-2,3-dihydro-2,2-dimethylbenzofuran (CAS 68298-46-4) and 1,1-dioxo-tetrahydro-2H-thiopyran-4-amine.

Example 18

N²-(3-Cyclopropyl-phenyl)-quinoline-2,5-diamine

The title compound, MS: m/e=276.4 (M+H$^+$), was prepared in accordance with the general method of example 1 from 5-nitro-2-chloroquinoline and 3-cyclopropylamine.

Example 19

Cyclopropanesulfonic acid {2-[(5-methyl-furan-2-ylmethyl)-amino]-quinolin-5-yl}-amide N²-(5-Methyl-furan-2-ylmethyl)-quinoline-2,5-diamine (200 mg, 0.79 mmol) was dissolved in 2 mL pyridine and cyclopropane sulfonylchloride (118 mg, 0.79 mmol) was added. The reaction mixture was stirred at room temperature overnight and quenched by addition of 50 mL water and acetic acid until pH 5. The mixture was extracted three times with ethyl acetate (50 mL each). The organic phases ware pooled, dried with sodium sulfate, filtered and evaporated. The residue was purified by flash chromatography on silica gel (cyclohexane/ethyl acetate 100:0->50:50 gradient). The title compound was obtained as a yellow oil (234 mg, 78%), MS: m/e=358.4 (M+H$^+$).

Example 20

N,N-dimethyl-N'-(2-{[(5-methyl-2-furyl)methyl]amino}quinolin-5-yl)sulfamide

The title compound, MS: m/e=361.0 (M+H$^+$), was prepared in accordance with the general method of example 19 from N²-(5-Methyl-furan-2-ylmethyl)-quinoline-2,5-diamine and dimethylsulfamoyl chloride.

Example 21

N,N-dimethyl-N'-{2-[(2-methyl-2,3-dihydro-1-benzofuran-7-yl)amino]quinolin-5-yl}sulfamide The title compound, MS: m/e=399.1 (M+H$^+$), was prepared in accordance with the general method of example 19 from N²-(2-methyl-2,3-dihydro-benzofuran-7-yl)-quinoline-2,5-diamine and dimethylsulfamoyl chloride.

Example 22

(2-Methoxy-benzyl)-(5-vinyl-quinolin-2-yl)-amine (5-Bromo-quinolin-2-yl)-(2-methoxy-benzyl)-amine (prepared from 5-bromo-2-chloroquinoline and 2-methoxybenzylamine as described in example 3, step A, 1 g, 2.9 mmol) was dissolved in 30 mL toluene. Vinyltributyltin (952 mg, 3.0 mmol) and tetrakis(triphenylphosphin)palladium (67 mg, 0.058 mmol) was added. The reaction mixture was refluxed overnight. The mixture was diluted with 100 mL acetonitrile and extracted three times with heptane (100 mL each). The acetonitrile phase was dried with sodium sulfate, filtered and evaporated. The residue was purified by flash chromatography on silica gel (heptane/ethyl acetate 100:0->80:20 gradient). The title compound was obtained as a yellow oil (544 mg, 64%), MS: m/e=291.3 (M+H$^+$).

Example 23

(5-Methyl-furan-2-ylmethyl)-(5-vinyl-quinolin-2-yl)-amine

The title compound, MS: m/e=265.3 (M+H$^+$), was prepared in accordance with the general method of example 22 from (5-bromo-quinolin-2-yl)-(5-methyl-furan-2-ylmethyl)-amine and vinyltributyltin.

Example 24

{2-[(5-Methyl-furan-2-ylmethyl)-amino]-quinolin-5-yl}-methanol

Step A: (5-Bromo-quinolin-2-yl)-(5-methyl-furan-2-ylmethyl)-amine (example 3, step A, 700 mg, 2.2 mmol) was dissolved in 30 mL tetrahydrofuran and cooled to −78° C. n-Butyllithium (3.45 mL, 1.6 M in hexane, 5.5 mmol) was added and the reaction mixture was allowed to warm to −10° C. Stirring was continued at −10° C. for 45 minutes. The reaction was cooled again to −78° C. and N,N-dimethylformamide (404 mg, 5.5 mmol) was added. The reaction mixture was slowly warmed up and quenched at 5° C. by addition of 100 mL water. The mixture was extracted three times with ethyl acetate (100 mL each). The organic phases were pooled, dried with sodium sulfate, filtered and evaporated. The residue was purified by flash chromatography on silica gel (heptane/ethyl acetate 100:0->50:50 gradient). 2-[(5-Methyl-furan-2-ylmethyl)-amino]-quinoline-5-carbaldehyde was obtained as a brown oil (242 mg, 41%), MS: m/e=267.1 (M+H$^+$).

Step B: 2-[(5-Methyl-furan-2-ylmethyl)-amino]-quinoline-5-carbaldehyde (150 mg, 0.56 mmol) was dissolved in 5 mL dichloroethan. Acetic acid (136 mg, 2.3 mmol) and sodium triacetoxy borohydride (258 mg, 1.2 mmol) were added. The reaction mixture was stirred at room temperature overnight and quenched by addition of 2N sodium carbonate solution (50 mL). The mixture was extracted three times with ethyl acetate (100 mL each). The organic phases were pooled, dried with sodium sulfate, filtered and evaporated. The residue was purified by flash chromatography on silica gel (heptane/ethyl acetate 100:0->50:50 gradient). The title compound was obtained as a light brown solid (105 mg, 69%), MS: m/e=269.5 (M+H$^+$).

Example 25

4-{2-[(5-Methyl-furan-2-ylmethyl)-amino]-quinolin-5-yl}-butyric acid methyl ester Step A: (5-Bromo-quinolin-2-yl)-(5-methyl-furan-2-ylmethyl)-amine (400 mg, 1.3 mmol) was dissolved in 4 mL N,N-dimethylformamide. Triethylamine (167 mg, 1.7 mmol), methyl-3-butenoate (173 mg, 1.7 mmol), tri-ortho-tolylphosphin (31 mg, 0.1 mmol) and palladium acetate (11 mg, 0.05 mmol) were added. The reaction mixture was heated at 120° C. for 1 hour and quenched by addition of 50 mL water. The mixture was extracted three times with ethyl acetate (100 mL each). The organic phases were pooled, dried with sodium sulfate, filtered and evaporated. The residue was purified by flash chromatography on silica gel (heptane/ethyl acetate 100:0->75:25 gradient). (E)-4-{2-[(5-Methyl-furan-2-ylmethyl)-amino]-quinolin-5-yl}-but-3-enoic acid methyl ester was obtained as a yellow oil (294 mg, 69%), MS: m/e=337.4 (M+H$^+$).

Step B: (E)-4-{2-[(5-Methyl-furan-2-ylmethyl)-amino]-quinolin-5-yl}-but-3-enoic acid methyl ester (290 mg, 0.86 mmol) was dissolved in 45 mL ethanol. Palladium on charcoal (10%, 92 mg, 0.086 mmol) was added and the reaction mixture war hydrogenated with a hydrogen balloon overnight. The palladium was filtered off and the solvent was evaporated. The title compound was obtained as a brown oil (256 mg, 88%), MS: m/e=339.1 (M+H$^+$).

Example 26

4-{2-[(5-Methyl-furan-2-ylmethyl)-amino]-quinolin-5-yl}-butan-1-ol

4-{2-[(5-Methyl-furan-2-ylmethyl)-amino]-quinolin-5-yl}-butyric acid methyl ester (100 mg, 0.3 mmol) was dissolved in 10 mL dry tetrahydrofurane. Lithiumborohydride (100 mg, 4.5 mmol) was added and the reaction mixture was refluxed overnight. The reaction mixture was quenched by addition of 1N hydrochloride solution and refluxed for 30 minutes. The mixture was then adjusted to pH 10 by addition of 25% solution of ammonium hydroxide and extracted three times with ethyl acetate (100 mL each). The organic phases were pooled, dried with sodium sulfate, filtered and evaporated. The residue was purified by flash chromatography on silica gel (heptane/ethyl acetate 100:0→0:100 gradient). The title compound was obtained as a light yellow oil (67 mg, 73%), MS: m/e=311.0 (M+H$^+$).

Example 27

N,N-Diethyl-4-{2-[(5-methyl-furan-2-ylmethyl)-amino]-quinolin-5-yl}-butyramide Diethylamine (89 mg, 1.22 mmol) was dissolved in 5 mL dioxane. Trimethylaluminium (2M solution in heptane, 0.61 mL, 1.22 mmol) was added and the mixture was stirred for 1 hour at room temperature. 4-{2-[(5-Methyl-furan-2-ylmethyl)-amino]-quinolin-5-yl}-butyric acid methyl ester (137 mg, 0.4 mmol) 7 mL dioxane was added and stirring was continued at 90° C. for 5 hours. The reaction mixture was quenched by addition of 0.6 mL water. The solvent was evaporated off. The residue was purified by flash chromatography on silica gel (heptane/ethyl acetate 100:0->0:100 gradient). The title compound was obtained as a yellow oil (40 mg, 26%), MS: m/e=380.5 (M+H$^+$).

Example 28

(2-Methoxy-benzyl)-[5-(2-methoxy-ethoxy)-quinolin-2-yl]-amine

Step A: 2-Chloro-quinolin-5-ol (CAS 124467-35-2) (0.3 g, 1.56 mmol) was dissolved in acetone (10 mL) and potassium carbonate (0.368 g, 2.75 mmol) was added. After addition of 2-bromethylmethylether (0.25 ml, 2.7 mmol) the reaction mixture was stirred for 18 h at 50° C. Then water was added and the mixture was extracted with ethyl acetate (3×). The combined organic phases were dried, filtered and concentrated. The residue was subjected to column chromatography (silica gel, heptane/ethyl acetate 9:1/4:1) to yield 2-chloro-5-(2-methoxy-ethoxy)-quinoline as a colourless oil (0.12 g, 30%). MS: m/e=238.8 (M+H$^+$)

Step B: 2-Chloro-5-(2-methoxy-ethoxy)-quinoline (100 mg, 0.35 mmol) and 2-methoxybenzylamine (144 mg, 1.05 mmol) were stirred in a sealed tube at 150° C. for 16 hours. The reaction mixture was purified by flash chromatography on silica gel (heptane/ethyl acetate 100:0->80:20 gradient). 5-(4-Fluorobenzyloxy)-quinolin-2-yl-(2-methoxy-benzyl)-amine was obtained as a yellow oil (57 mg, 42%), MS: m/e=339.3 (M+H$^+$).

Example 29

(2-Methoxy-benzyl)-(5-methoxy-quinolin-2-yl)-amine

The title compound, MS: m/e=295.4 (M+H$^+$), was prepared in accordance with the general method of example 1 from 5-methoxy-2-chloroquinoline (CAS-RN: 160893-07-2) and 2-methoxybenzylamine.

Example 30

(2-Methoxy-benzyl)-[5-(2-methylsulfanyl-ethoxy)-quinolin-2-yl]-amine

Step A: (5-Iodo-quinolin-2-yl)-(2-methoxy-benzyl)-amine, MS: m/e=391.4 (M+H$^+$), was prepared in accordance with the general method of example 3, Step A from 5-iodo-2-chloroquinoline (CAS-RN: 455955-26-7) and 2-methoxy-benzylamine.

Step B: (5-Iodo-quinolin-2-yl)-(2-methoxy-benzyl)-amine (0.3 g, 1.0 mmol) was dissolved in toluene (2 mL). After addition of 2-hydroxyethyl-methylsulfid (130 μL, 2.0 mmol), CuI (15 mg, 0.1 mmol), phenantroline (28 mg, 0.2 mmol) and caesium carbonate (0.5 g, 2.0 mmol) the reaction mixture was heated to 100° C. for 72 h. Then water was added and the mixture twice extracted with toluene. The combined organic phases were dried on sodium sulfate and evaporated. The residue was subjected to column chromatography (silica gel; heptane, ethyl acetate 10:0->3:2) to yield the title compound (75 mg, 26%) as a brown oil; MS: m/e=355.6 (M+H$^+$).

Example 31

N-Hydroxy-2-[(5-methyl-furan-2-ylmethyl)-amino]-quinoline-carboxamidine

Step A: (5-Iodo-quinolin-2-yl)-(5-methyl-furan-2-ylmethyl)-amine, MS (ISP): m/e=365.0 (M+H$^+$), was prepared from 5-iodo-2-chloroquinoline (CAS 455955-26-7) and 5-methyl-2-furanmethanamine as described in example 3 step A.

Step B: A stirred mixture of (5-iodo-quinolin-2-yl)-(5-methyl-furan-2-ylmethyl)-amine (example 50, step A) (500 mg, 1.37 mmol), zinc cyanide (177 mg, 1.5 mmol) and tetrakis-(triphenylphosphine)-palladium (159 mg, 0.14 mmol) in dimethylformamide (5 ml) was heated at 160° C. for 15 min in a microwave reactor. The reaction mixture was poured into water (15 ml) and extracted with ethyl acetate (2×10 ml). The combined organic layers were washed with brine (10 ml), dried (MgSO$_4$) and evaporated. The crude product was purified by flash chromatography (ethyl acetate/ heptane) on silica gel to yield 2-[(5-methyl-furan-2-ylmethyl)-amino]-quinoline-5-carbonitrile as light brown solid (346 mg, 91%). M.p. 102° C.; MS (ISN): m/e=262.0 (M−H$^-$).

Step C: N-Hydroxy-2-[(5-methyl-furan-2-ylmethyl)-amino]-quinoline-carboxamidine, white foam; MS (ISP): m/e=297.3 (M+H$^+$), was prepared from 2-[(5-methyl-furan-2-ylmethyl)-amino]-quinoline-5-carbonitrile and hydroxylamine hydrochloride as described in example 32 step C.

Example 32

N-Hydroxy-2-(2-methoxy-benzylamino)-quinoline-5-carboxamidine

Step A: (5-Iodo-quinolin-2-yl)-(2-methoxy-benzyl)-amine, light brown oil; MS (ISP): m/e=391.0 (M+H$^+$), was prepared from 5-iodo-2-chloroquinoline (CAS 455955-26-7) and 2-methoxybenzylamine as described in example 3 step A.

Step B: 2-(2-Methoxy-benzylamino)-quinoline-5-carbonitrile, light yellow solid; MS (ISN): m/e=288.3 (M−H$^-$); m.p. 133° C., was prepared from (5-iodo-quinolin-2-yl)-(2-methoxy-benzyl)-amine as described in example 31 step A.

Step C: A stirred suspension of 2-(2-methoxy-benzylamino)-quinoline-5-carbonitrile (example 136, step B) (289 mg, 1.0 mmol), hydroxylamine hydrochloride (257 mg, 3.7 mmol) and sodium carbonate (212 mg, 2.0 mmol) in ethanol (4 ml) and water (4 ml) was heated under reflux conditions for 17 h, water (5 ml) was added, the precipitate was collected by filtration, washed with water and heptane and dried to yield the crude product as solid which was further purified by crystallization (diethyl ether/ methanol) to yield N-hydroxy-2-(2-methoxy-benzylamino)-quinoline-5-carboxamidine as off-white solid (290 mg, 90%). MS (ISP): m/e=323.2 (M+H$^+$); m.p. 161° C.

The invention claimed is:
1. A compound of formula (I)

I wherein
Z is a bond, —CH$_2$—, or —CHCH$_3$—;
R$^1$ is alkyl, hydroxyalkyl, haloalkyl, aminoalkyl, cyanoalkyl, cycloalkyl, allyl, -alkylene-C(O)Oalkyl, -alkylene-C(O)NR$^i$R$^{ii}$, —C(N—R$^{iii}$)NR$^{iv}$R$^v$, —C(=N—R$^{iii}$)-cycloalkyl, —C(=N—R$^{iii}$)-alkyl, —O-alkyl, —O-cycloalkyl, —O-alkylene-O-alkyl, —O-alkylene-S(O)$_x$-alkyl, or —NR$^a$R$^b$, wherein R$^a$ and R$^b$ are each independently H, alkyl, cycloalkyl, -alkylene-cycloalkyl, allyl, -alkylene-S(O)$_x$-alkyl, —S(O)$_2$NR$^{vi}$R$^{vii}$, —S(O)$_2$-alkyl, —S(O)$_2$-cycloalkyl, -alkylene-NR$^{viii}$R$^{ix}$, -alkylene-O-alkyl, —C(O)-cycloalkyl, —C(O)alkyl, —C(O)-alkylene-heterocycloalkyl, —C(O)-heterocycloalkyl, —C(O)NR$^{vi}$R$^{vii}$, —C(O)-alkylene-NR$^{viii}$R$^{ix}$, —C(O)-alkylene-O-alkyl, or heterocycloalkyl;
Ar$^1$ is phenyl or 5- to 10-membered mono- or bicyclic heteroaryl, each unsubstituted or substituted with one or more alkyl, cycloalkyl, alkoxy, haloalkoxy, haloalkyl, halo, OH, CN, NH$_2$, NO$_2$, or having two substituents in the ortho-position that form a bridge anellated to the aromatic ring, wherein the bridge is selected from —O—CH$_2$CH$_2$O—, —O—CHCH$_3$CH$_2$—, and —O—C(CH$_3$)$_2$CH$_2$—, and wherein phenyl is not substituted with halo in para-position;
R$^i$, R$^{ii}$, R$^{vi}$, R$^{vii}$, R$^{viii}$ and R$^{ix}$ are each independently H, alkyl, cycloalkyl, or -alkylene-N(alkyl)$_2$;
R$^{iii}$, R$^{iv}$, and R$^v$ are each independently H, OH or alkoxy;
x is 0, 1 or 2; and
heterocycloalkyl is unsubstituted or substituted with one or more oxo, alkyl, halo, haloalkyl, haloalkoxy, alkoxy, hydroxy, hydroxyalkyl, or CN,
or a pharmaceutically acceptable salt thereof.

2. The compound of claim 1, wherein
R$^1$ is alkyl, hydroxyalkyl, haloalkyl, aminoalkyl, cyanoalkyl, cycloalkyl, allyl, -alkylene-C(O)Oalkyl, -alkylene-C(O)NR$^i$R$^{ii}$, —C(N—R$^{iii}$)NR$^{iv}$R$^v$, —O-alkyl, —O-cycloalkyl, —O-alkylene-O-alkyl, —O-alkylene-S(O)$_x$-alkyl, or —NR$^a$R$^b$, wherein R$^a$ and R$^b$ are each independently H, alkyl, cycloalkyl, -alkylene-cycloalkyl, allyl, -alkylene-S(O)$_x$-alkyl, —S(O)$_2$NR$^{vi}$R$^{vii}$, —S(O)$_2$-alkyl, —S(O)$_2$-cycloalkyl, -alkylene-NR$^{viii}$R$^{ix}$, -alkylene-O-alkyl, or heterocycloalkyl;
R$^i$, R$^{ii}$, R$^{vi}$, R$^{vii}$, R$^{viii}$ and R$^{ix}$ are each independently H, alkyl, cycloalkyl, or -alkylene-N(alkyl)$_2$;
R$^{iii}$, R$^{iv}$, and R$^v$ are each independently H, OH or alkoxy; and
x is 0, 1 or 2, wherein
heterocycloalkyl is unsubstituted or substituted with one or more oxo, alkyl, halo, haloalkyl, haloalkoxy, alkoxy, hydroxy, hydroxyalkyl, or CN.

3. The compound of claim 2, wherein
R$^1$ is alkyl, hydroxyalkyl, allyl, -alkylene-C(O)Oalkyl, -alkylene-C(O)NR$^i$R$^{ii}$, —C(N—R$^{iii}$)NR$^{iv}$R$^v$, —O-alkyl, —O-alkylene-O-alkyl, —O-alkylene-S(O)$_x$-alkyl,
or —NR$^a$R$^b$, wherein R$^a$ and R$^b$ are each independently H, alkyl, allyl, -alkylene-S(O)$_x$-alkyl, —S(O)$_2$NR$^{vi}$R$^{vii}$, —S(O)$_2$-cycloalkyl, -alkylene-O-alkyl, or heterocycloalkyl;
R$^i$, R$^{ii}$, R$^{vi}$ and R$^{viii}$ are each independently H, alkyl, cycloalkyl, or alkylene-N(alkyl)$_2$;
R$^{iii}$, R$^{iv}$, and R$^v$ are each independently H, OH or alkoxy; and
x is 0, 1 or 2, wherein
heterocycloalkyl is unsubstituted or substituted with one or more oxo, alkyl, halo, haloalkyl, haloalkoxy, alkoxy, hydroxy, hydroxyalkyl, or CN.

4. The compound of claim 1, wherein
R$^i$, R$^{ii}$, R$^{vi}$, R$^{vii}$, R$^{viii}$ and R$^{ix}$ are each independently H, alkyl, cycloalkyl, or -alkylene-N(alkyl)$_2$.

5. The compound of claim 4, wherein R$^i$, R$^{ii}$, R$^{vi}$, R$^{vii}$, R$^{viii}$ and R$^{ix}$ are alkyl.

6. The compound of claim 1, wherein R$^{iii}$, R$^{iv}$, and R$^v$ are each independently H, OH or alkoxy.

7. The compound of claim 6, wherein, $R^{iii}$, $R^{iv}$, and $R^v$ are each independently H or OH.

8. The compound of claim 1, wherein heterocycloalkyl is unsubstituted or substituted with one or more oxo, alkyl, halo, haloalkyl, haloalkoxy, alkoxy, hydroxy, hydroxyalkyl, or CN.

9. The compound of claim 8, wherein the substitutents are oxo or alkyl.

10. The compound of claim 1, wherein heterocycloalkyl is selected from the group consisting of pyrrolidinyl, tetrahydrothiophenyl, tetrahydropyranyl, tetrahydrothiopyranyl, piperidinyl, piperazinyl, morpholinyl, and thiomorpholinyl.

11. The compound of claim 10, wherein heterocycloalkyl is selected from the group consisting of tetrahydropyranyl, tetrahydrothiopyranyl and piperidinyl.

12. The compound of claim 1, wherein Z is a bond or —CH$_2$—.

13. The compound of claim 1, wherein
Ar$^1$ is phenyl or a 5- to 10-membered mono- or bicyclic heteroaryl, each unsubstituted or substituted with one or more alkyl, cycloalkyl, alkoxy, haloalkoxy, haloalkyl, OH, CN, NH$_2$, NO$_2$, or having two substituents in the ortho-position that form a bridge anellated to the aromatic ring, wherein the bridge is selected from —O—CH$_2$CH$_2$O—, —O—CHCH$_3$CH$_2$—, and —O—C(CH$_3$)$_2$CH$_2$—.

14. The compound of claim 1 wherein
Ar$^1$ is phenyl or a 5- to 10-membered mono- or bicyclic heteroaryl, each unsubstituted or substituted with one or more alkyl, cycloalkyl, alkoxy, haloalkoxy, or having two substituents in the ortho-position that form a bridge anellated to the aromatic ring, wherein the bridge is selected from —O—CH$_2$CH$_2$O—, —O—CHCH$_3$CH$_2$—, and —O—C(CH$_3$)$_2$CH$_2$—.

15. The compound of claim 1, wherein
Ar$^1$ is phenyl or a 5- to 10-membered mono- or bicyclic heteroaryl,
wherein phenyl is unsubstituted or substituted with one or more alkyl, cycloalkyl, alkoxy, haloalkoxy, haloalkyl, OH, CN, NH$_2$, NO$_2$, or having two substituents in the ortho-position that form a bridge anellated to the aromatic ring, wherein the bridge is selected from —O—CH$_2$CH$_2$O—, —O—CHCH$_3$CH$_2$—, and —O—C(CH$_3$)$_2$CH$_2$—, and
wherein the 5- to 10-membered mono- or bicyclic heteroaryl is unsubstituted or substituted with one or more alkyl, cycloalkyl, alkoxy, haloalkoxy, halo, haloalkyl, OH, CN, NH$_2$, or NO$_2$.

16. The compound of claim 1, wherein
Ar$^1$ is phenyl or a 5- to 10-membered mono- or bicyclic heteroaryl,
wherein phenyl is unsubstituted or substituted with one or more alkyl, cycloalkyl, alkoxy, haloalkoxy, or having two substituents in the ortho-position that form a bridge anellated to the aromatic ring, wherein the bridge is selected from —O—CH$_2$CH$_2$O—, —O—CHCH$_3$CH$_2$—, and —O—C(CH$_3$)$_2$CH$_2$—, and
wherein the 5- to 10-membered mono- or bicyclic heteroaryl is unsubstituted or substituted with one or more alkyl, cycloalkyl, alkoxy, or haloalkoxy.

17. The compound of claim 16, wherein the 5- to 10-membered mono- or bicyclic heteroaryl is selected from the group consisting of thiophenyl, furanyl, pyrrolyl, imidazolyl, pyrazolyl, oxazolyl, isoxazolyl, thiazolyl, isothiazolyl, [1,2,4]oxadiazolyl, [1,3,4]oxadiazolyl, [1,2,4]triazolyl, [1,2,3]triazolyl, tetrazolyl, pyridinyl, pyrimidinyl, pyrazinyl, pyridazinyl, indolyl, benzofuranyl and benzothiofuranyl.

18. The compound of claim 17, wherein heteroaryl is selected from the group consisting of furanyl and benzofuranyl.

19. The compound of claim 1, wherein Ar$^1$ is selected from the group consisting of 5-methyl-furan-2-yl, 2-methoxy-phenyl, 2-methyl-benzofuran-7-yl, 2-trifluoromethoxy-phenyl, 2-methyl-2,3-dihydro-benzofuran-7-yl, 2,2-dimethyl-2,3-dihydro-benzofuran-7-yl, and 3-cyclopropyl-phenyl.

20. The compound of claim 1, selected from the group consisting of
N$^2$-(2-Methoxy-benzyl)-quinoline-2,5-diamine;
N$^2$-(5-Methyl-furan-2-ylmethyl)-quinoline-2,5-diamine;
N$^2$-(5-Methyl-furan-2-ylmethyl)-N$^5$-(1-methyl-piperidin-4-yl)-quinoline-2,5-diamine;
N$^5$-(2-Methoxy-ethyl)-N$^2$-(5-methyl-furan-2-ylmethyl)-quinoline-2,5-diamine;
N$^5$-Methyl-N$^2$-(5-methyl-furan-2-ylmethyl)-quinoline-2,5-diamine;
N$^5$-Allyl-N$^2$-(5-methyl-furan-2-ylmethyl)-quinoline-2,5-diamine;
N$^2$-(5-Methyl-furan-2-ylmethyl)-N$^5$-(tetrahydro-pyran-4-yl)-quinoline-2,5-diamine;
N$^5$-(3-Methoxy-propyl)-N$^2$-(5-methyl-furan-2-ylmethyl)-quinoline-2,5-diamine;
N$^2$-(5-Methyl-furan-2-ylmethyl)-N$^5$-(2-methylsulfanyl-ethyl)-quinoline-2,5-diamine; and
N$^5$-(2-Methanesulfinyl-ethyl)-N$^2$-(5-methyl-furan-2-ylmethyl)-quinoline-2,5-diamine.

21. The compound of claim 1, selected from the group consisting of
N$^5$-(2-Methanesulfonyl-ethyl)-N$^2$-(5-methyl-furan-2-yl-methyl)-quinoline-2,5-diamine;
N$^2$-(2-Methyl-benzofuran-7-yl)-N$^5$-(2-methylsulfanyl-ethyl)-quinoline-2,5-diamine;
N$^2$-(2-Trifluoromethoxy-benzyl)-quinoline-2,5-diamine;
N$^2$-(2-Methyl-benzofuran-7-yl)-quinoline-2,5-diamine;
N$^2$-(2-Methyl-2,3-dihydro-benzofuran-7-yl)-quinoline-2,5-diamine;
N$^2$-(2,2-Dimethyl-2,3-dihydro-benzofuran-7-yl)-quinoline-2,5-diamine;
N$^2$-(2,2-Dimethyl-2,3-dihydro-benzofuran-7-yl)-N$^5$-(1,1-dioxo-hexahydro-1λ$^6$-thiopyran-4-yl)-quinoline-2,5-diamine;
N$^2$-(3-Cyclopropyl-phenyl)-quinoline-2,5-diamine;
Cyclopropanesulfonic acid {2-[(5-methyl-furan-2-ylmethyl)-amino]-quinolin-5-yl}-amide;
N,N-dimethyl-N'-(2-{[(5-methyl-2-furyl)methyl]amino}quinolin-5-yl)sulfamide; and
N,N-dimethyl-N'-{2-[(2-methyl-2,3-dihydro-1-benzofuran-7-yl)amino]quinolin-5-yl}sulfamide.

22. The compound of claim 1, selected from the group consisting of
(2-Methoxy-benzyl)-(5-vinyl-quinolin-2-yl)-amine;
(5-Methyl-furan-2-ylmethyl)-(5-vinyl-quinolin-2-yl)-amine;
{2-[(5-Methyl-furan-2-ylmethyl)-amino]-quinolin-5-yl}-methanol;
4-{2-[(5-Methyl-furan-2-ylmethyl)-amino]-quinolin-5-yl}-butyric acid methyl ester;
4-{2-[(5-Methyl-furan-2-ylmethyl)-amino]-quinolin-5-yl}-butan-1-ol;
N,N-Diethyl-4-{2-[(5-methyl-furan-2-ylmethyl)-amino]-quinolin-5-yl}-butyramide;
(2-Methoxy-benzyl)-[5-(2-methoxy-ethoxy)-quinolin-2-yl]-amine;

(2-Methoxy-benzyl)-(5-methoxy-quinolin-2-yl)-amine;
(2-Methoxy-benzyl)-[5-(2-methylsulfanyl-ethoxy)-quinolin-2-yl]-amine;
N-Hydroxy-2-[(5-methyl-furan-2-ylmethyl)-amino]-quinoline-carboxamidine; and
N-Hydroxy-2-(2-methoxy-benzylamino)-quinoline-5-carboxamidine.

23. A pharmaceutical composition comprising a therapeutically effective amount of a compound of formula I

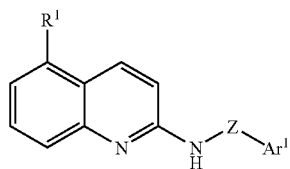

I wherein
Z is a bond, —CH$_2$—, or —CHCH$_3$—;
R$^1$ is alkyl, hydroxyalkyl, haloalkyl, aminoalkyl, cyanoalkyl, cycloalkyl, allyl, -alkylene-C(O)Oalkyl, -alkylene-C(O)NR$^i$R$^{ii}$, —C(N—R$^{iii}$)NR$^{iv}$R$^v$, —C(=N—R$^{iii}$)-cycloalkyl, —C(=N—R$^{iii}$)-alkyl, —O-alkyl, —O-cycloalkyl, —O-alkylene-O-alkyl, —O-alkylene-S(O)$_x$-alkyl, or —NR$^a$R$^b$, wherein R$^a$ and R$^b$ are each independently H, alkyl, cycloalkyl, -alkylene-cycloalkyl, allyl, -alkylene-S(O)$_x$-alkyl, —S(O)$_2$NR$^{vi}$R$^{vii}$, —S(O)$_2$-alkyl, —S(O)$_2$-cycloalkyl, -alkylene-NR$^{viii}$R$^{ix}$, -alkylene-O-alkyl, —C(O)-cycloalkyl, —C(O)alkyl, —C(O)-alkylene-heterocycloalkyl, —C(O)-heterocycloalkyl, —C(O)NR$^{vi}$R$^{vii}$, —C(O)-alkylene-NR$^{viii}$R$^{ix}$, —C(O)-alkylene-O-alkyl, or heterocycloalkyl;

Ar$^1$ is phenyl or 5- to 10-membered mono- or bicyclic heteroaryl, each unsubstituted or substituted with one or more alkyl, cycloalkyl, alkoxy, haloalkoxy, haloalkyl, halo, OH, CN, NH$_2$, NO$_2$, or having two substituents in the ortho-position that form a bridge anellated to the aromatic ring, wherein the bridge is selected from —O—CH$_2$CH$_2$O—, —O—CHCH$_3$CH$_2$—, and —O—C(CH$_3$)$_2$CH$_2$—, and wherein phenyl is not substituted with halo in para-position;

R$^i$, R$^{ii}$, R$^{vi}$, R$^{vii}$, R$^{viii}$ and R$^{ix}$ are each independently H, alkyl, cycloalkyl, or -alkylene-N(alkyl)$_2$;

R$^{iii}$, R$^{iv}$, and R$^v$ are each independently H, OH or alkoxy;

x is 0, 1 or 2; and heterocycloalkyl is unsubstituted or substituted with one or more oxo, alkyl, halo, haloalkyl, haloalkoxy, alkoxy, hydroxy, hydroxyalkyl, or CN, or a pharmaceutically acceptable salt thereof and a pharmaceutically acceptable carrier.

* * * * *